United States Patent [19]
Bühring et al.

[11] Patent Number: 6,143,296
[45] Date of Patent: Nov. 7, 2000

[54] ANTIBODY 67D2

[75] Inventors: Hans-Jörg Bühring, Tübingen, Germany; Suzanne M. Watt, London, United Kingdom

[73] Assignee: Eberhard-Karls-Universitat Tubinger, Germany

[21] Appl. No.: 09/105,898

[22] Filed: Jun. 26, 1998

[30] Foreign Application Priority Data

Jun. 30, 1997 [DE] Germany .............................. 197 27 813

[51] Int. Cl.[7] ........................ A61K 39/395; C07K 16/28; C07K 16/30; C12N 5/16; G01N 33/53
[52] U.S. Cl. ..................................... 424/141.1; 424/153.1; 424/155.1; 424/156.1; 424/178.1; 530/388.85; 530/391.7; 530/391.3; 435/344.1; 435/810; 435/975
[58] Field of Search ........................... 530/388.15, 388.7, 530/388.8, 388.85; 435/326, 332, 344, 344.1, 810, 875; 424/130.1, 138.1, 172.1, 173.1, 174.1, 178.1

[56] References Cited

PUBLICATIONS

Pancino, G. et al. Characterization and distribution in human tissues of a glycoproteic antigen defined by monoclonal antibody 1BE12 raised against the human breast cancer cell line T47D. Cancer Research, 50: 7333–7342, 1990.

Pancino, G. et al. A novel monoclonal antibody (7B10) with differential reactivity between human mammary carcinoma and normal breast. Cancer Research, 47: 4444–4452, 1987.

*Primary Examiner*—Yvonne Eyler
*Assistant Examiner*—Anne L. Holleran
*Attorney, Agent, or Firm*—Oppenheimer, Wolff & Donnelly, LLP; Claude A. S. Hamrick

[57] ABSTRACT

A monoclonal antibody specific to the cell surface glycoprotein CD164 is designated 67D2 and produced by hybridoma cells deposited under No. DSM ACC2303 at the German Collection of Microorganisms and Cell Cultures Ltd., DSMZ.

6 Claims, No Drawings

ANTIBODY 67D2

BACKGROUND OF THE INVENTION

1. Field of the Invention

The invention relates to a monoclonal antibody specifically directed against CD164.

2. Related Prior Art

Such antibodies are known from DE 195 30 272 C1 and DE 195 30 273.

CD164 is a glycosylated cell surface protein that originally has been identified as peanut agglutinin-(PNA)-binding glycoprotein.

Malignant cells of a number of human tumors have peanut agglutinin(PNA)-binding glycoproteins on their cell surface. These PNA-binding glycoproteins offer inter alia the possibility of bringing detection agents and/or therapeutically effective agents directly onto the corresponding cells and of binding these to them. The glycoproteins MUC1, MUC2 and MUC3, named according to the MUC nomenclature which has in the meantime been introduced, have been known for a number of years. A recently identified cell surface glycoprotein is the protein MGC-24, whose amino acid sequence and corresponding nucleotide sequence have been fully identified by Masuzawa et. al., J. BIOCHEM. 112, 609–615 (1992).

Recently, a variant or isoform of the protein MGC-24 has been found, designated MGC-24v. MGC-24 and MGC-24v are almost completely identical in their extracellular domains. However, MGC-24 is a predominantly secreted protein whereas MGC-24v is a type I integral membrane protein. With its molecular weight of 160 kDa MGC-24v is a homodimer of two 80 kDa subunits.

In a CD classification the glycoprotein MGC-24v was designated CD164, which designation will be used hereinafter.

The function of CD164 is still completely unknown. However, this cell surface protein is being expressed by a variety of neoplastic epithelial tissues. Therefore, it is ideally suited as a target point for a specific cellular diagnosis and therapy of such tumors.

Especially in antibody specifically binding to CD164 could be a mediator for a corresponding targeted diagnostic or therapeutic agent.

Such an antibody can be linked to both simple detection agents such as fluorescent dyes or radioactive materials as well as special, therapeutically-effective agents.

DE 195 30 272 C1 discloses a monoclonal antibody binding to MGC-24 and being designated 103B2. A further antibody against MGC-24 is disclosed in DE 195 30 273 C1. This antibody is designated 105A5. In the meantime it has turned out that both antibodies also identify the isoform MGC-24v, i.e. CD164 (Zannettino et al., "CD164 Workshop Panel Report", in: Leucocyte Typing VI, Kishimoto, T., et al., Garland Publishing, New York (in press)).

For detecting and targeted influencing the antigen it is desired to have different monoclonal antibodies available so that results can experimentally be verified with high probability.

Further, different monoclonal antibodies directed against the same antigen can differ with respect to their sensitivities and cross reactivities. In case several monoclonal antibodies against a given antigen are available, the antibody suited best can be chosen depending from the application.

Antibody 103B2, disclosed in DE 195 30 272 C1 is of immunoglobulin class IgG3 whereas antibody 105A5, disclosed in DE 195 30 273 C1 is of immunoglobulin class IgGM.

Antibodies, i.e. immunoglobulins, are comprised of variable regions having the function of specific epitope recognition, as well as of constant regions being characteristic for a immunoglobulin class. The constant regions of the antibodies have a substantial influence on their characteristics, too. Antibodies of immunoglobulin class IgM form tetrameric structures whereas antibodies of IgG class are monomeric. Further, there are four different subclasses of immunoglobulin class IgG which differ with respect to their disulfide bridge binding, their stability and further physiochemical properties.

The heterogeneity of the constant regions of the immunoglobulins is being used above all with the today usual indirect detection methods wherein antibodies are detected by secondary antibodies linked to detecting agents. These secondary antibodies bind specifically to the constant regions of the primary antibodies binding to the antigens. Secondary antibodies in most cases detect thus only one immunoglobulin class.

SUMMARY OF THE INVENTION

Therefore, it is appropriate to have monoclonal antibodies of different immunoglobulin classes available in order to be able to make use of a as broad as possible variety of assay techniques.

Therefore, it is an object of the present invention to provide a further monoclonal antibody binding specifically to CD164 and being available in practically unlimited amounts.

This object is achieved by the provision of a monoclonal antibody produced and released by hybridoma cells deposited on or about Mar. 20, 1997 at the International Depository Authority DSMZ-Deutsche Sammlung Von Mikroorganismen Und Zellkulturen Gmbh (German Collection of Microorganisms and Cell Cultures, Ltd. (DSMZ)), Mascheroder Weg 1b, D-38124 Braunschweig Germany under No. DSM ACC2303 with the German Collection of Microorganisms and Cell Cultures, Ltd., DSMZ. It has been given to the designation 67D2.

In the course of the analyses in connection with the monoclonal antibody 67D2 it could be shown that it is of immunoglobulin class IgG1 (see in this connection example 1 below). Therefore, with this monoclonal antibody an antibody with up to now not available subtype has been provided that can be reproduced in standardized manner, can be produced in potentially unlimited quantities and binds specifically to the cell surface glycoprotein CD164.

The antibody according to the invention allows a targeted detection and treatment of cells expressing CD164. It thus represents a further versatile means for physicians and scientists for on the one hand identifying such cells, both in cell culture and patient organism, and on the other hand for possibly manipulating these cells either by the antibody itself or specific agents linked to the latter or to a suitable secondary antibody.

The invention further relates to hybridoma cells deposited under No. DSM ACC2303 with the German Collection of Microorganism and Cell Cultures, Ltd., DSMZ, and producing the antibody with the designation 67D2.

Further, the invention relates to a method for producing hybridoma cells synthesizing and releasing an antibody directed against cell surface glycoprotein CD164. This method comprises the steps generally known in the art, as described for example by Bühring et al. in Hybridoma 1991, Volume 10, No. 1, pp. 77–78:

1. immunization or sensitization of an animal, preferably a mouse of the Balb/c line, with the antigen or immunogen;

2. collecting the antibody-producing cells, preferably the lymphocytes of the spleen of that animal;
3. fusion of these antibody-producing cells with a stable, immortalized cell line, preferably a myeloma cell line, to hybridoma cells; and
4. isolation and multiplication (cloning) of such hybridoma cells that secrete an antibody binding to the antigen.

The method in accordance with the invention is characterized in that the animal is immunized with cells of the breast cancer cell line T-47D (American Type Culture Collection, ATCC No. HTB133).

In this connection it turned out to be an advantage that this cell line presents a strong expression of CD164, as has been shown during the experiments leading to antibody 67D2.

When screening hybridoma cells producing antibodies specific for CD164, it is preferred during isolation of the hybridoma cells, if only those hybridoma cells are selected which produce antibodies with a specification for a cell line previously transfected with the cDNA for CD164.

The production of such a cell line is described in example 2 below.

This transfected cell line is specifically advantageous for selecting the hybridoma cells since it expresses huge quantities of CD164 on their cell surface.

The invention also relates to the use of the antibody of the invention for diagnostic and/or therapeutic treatment of tumors, in particular gastric, colon and breast carcinoma.

Tumor cells, in particular gastric, colon and breast carcinoma cells are characterized by a comparably high content of cell surface glycoprotein CD164. An antibody according to the invention coupled with a detecting means, for instance a radio active marker, indirectly binds this detecting means to the respective cells and thus allows the direct detection of these cells, for example using x-ray diagnostic/scintigraphic methods. Therefore, a very early diagnosis of tumors is possible, under certain circumstances even in vivo.

In an analogues way the antibody may be coupled to a therapeutically active agent and therefore allow a direct and targeted modulation or even elimination of CD164 carrying cells, particularly tumor cells.

In a preferred embodiment the antibody produced and released by hybridoma cells deposited under No. DSM ACC2303 with the German Collection of Microorganisms and Cell Cultures, Ltd., DSMZ, is being used for such a diagnostic and/or therapeutic treatment.

In order to facilitate the therapeutic and/or diagnostic application of the inventive antibody, the antibody may be mixed in a pharmaceutical composition with adequate accessory substances. Consequently, the invention also relates to a pharmaceutical agent for diagnostic and/or therapeutic treatment of tumors, comprising the inventive antibody binding to CD164 and produced and released by hybridoma cells deposited under No. DSM ACC2303 at the German Collection of Microorganisms and Cell Cultures, Ltd. (DSMZ).

Using an inventive antibody cells carrying CD164 may be detected in a suspension of different cells using the methods known in the art, for instance the enzyme-linked immunosorbent assay, ELISA, or the radioimmuno assay, RIA. The present invention therefore also relates to a kit for the detection of the cell surface glycoprotein CD164 comprising antibody 67D2.

In connection with the present invention, it has surprisingly been found that the monoclonal antibody with the designation 67D2 and produced by hybridoma cells deposited under No. DSM ACC2303 at the German Collection of Microorganisms and Cell Cultures, Ltd. binds to a subpopulation of mononuclear bone marrow cells.

The invention therefore also relates to the use of antibody 67D2 for detection of haematopoietic cells, as well as to a kit for the detection of haematopoietic cells, comprising antibody 67D2. It is thereby possible to select and purify undifferentiated CD34$^+$ subpopulations from bone marrow for functional analyses.

Further advantages can be taken from the following description.

It is understood that the afore-mentioned features and those to be explained below can be used not only in the specified combinations but also in other combinations or alone without going beyond the scope of the present invention.

DETAILED DESCRIPTION

The invention is explained in more detail in the following on the basis of application examples and embodiments.

EXAMPLE 1

Production and Characterization of Monoclonal Antibodies Against the Cell Surface Glycoprotein CD164

Cells of the breast cancer cell line T-47D commercially available under ATCC No. HTB133 are used as antigen.

Eight week-old Balb/c mice are immunized intraperitoneally twice, at intervals of 10 days with $10^7$ cells from cell line T-47D. Four days before the fusion $5 \times 10^5$ cells were applied directly into the spleen to strengthen the immunologic response.

The production of antibodies in the mouse organism is tested by screening the blood serum of the affected animal for binding properties with the antigen using the ELISA test familiar to experts.

After approx. 3 weeks the lymphocytes of the successfully immunized animal are collected by surgically removing the spleen and disintegrating it into a cell suspension.

The suspended spleen cells are fused with myeloma cells from the known strain SP2/0 in the presence of polyethylene glycol. The fusion culture is cultivated in a medium containing hypoxanthine, aminopterine and thymidine (HAT medium), in this case HAT-RPMI-1640, in which only hybrid cells can grow since these have both the property of myeloma cells to divide infinitely, and the property of the antibody-producing lymphocytes to grow in a medium containing HAT.

Following fusion the cells are plated in microtiter plates and incubated at 37 C, 5% $CO_2$.

The culture supernatants are screened after 10–14 days on the T-47D cell line in a flow cytometer. In a second stage the supernatants are tested for a reaction with a cell line that has previously been transfected with cDNA for CD164. The production of this transfected cell line will be described below in example 2. Hybridoma cells producing antibodies with a specification for these cell lines are selected, isolated and cultivated, i.e. cloned, according to the known limited dilution method.

This screening strategy benefits from the fact that the transfected cell line expresses great quantities of CD164 on its cell surface.

Positively reacting hybridoma cell cultures are subjected to further cultivation, the antibodies are concentrated, purified and characterized.

The monoclonal antibody 67D2 was obtained at the end of the foregoing screening strategy. With the PE-conjugated anti-isotype-specific antiserum, the isotype was determined as IgG1 by means of direct immunofluorescence.

The production, purification and characterization of the antibodies was carried out using methods familiar to the person skilled in the art.

The antibody 67D2, produced by the hybridoma cell registered at the German Collection of Microorganisms and Cell Cultures Ltd., DSMZ, under the number DSM ACC 2303, has the following characteristic features:

Immunoglobulin class: IgG1
specific binding affinity to: CD164

EXAMPLE 2

Production of a CD164 Expressing Cell Line

During the experiment leading to the identification of the antigen of monoclonal antibody 103B2 (DE 195 30 272 C2) a CD164 expressing cell line was established. Those experiments were to find and analyze the respective gene.

In order to isolate the gene coding for the antigen detected by monoclonal antibody 103B2, a retro-viral expression library was constructed according to the method described by Rayner and Gondo in Mol.Cell.Biol. 1994, Vol. 14, page 880. With this method mRNA from cultured stroma cells of human marrow was used.

cDNA transcripts were directionally cloned in the retroviral plasmid vector pRUF.Neo. DNA from the library was used to transfect an amphotropic packaging cell line (PA317). Transiently generated retroviral particles were harvested and used for a stable infection of an ecotropic packaging cell line. Viruses produced from these cells were then used to infect the factordependent murinic haematopoietic cell line FDC-P1.

Infected FDC-P1 cells were selected for G418-resistance, and cells which express the antigen detected by the antibody 103B2 were isolated and enriched. The multiplication of the cells detected by the antibody was carried out using multiple rounds of an immuno-magnetic cell sorting (Dynabeads). Following this FACS sorting clonal populations of the transfected cells were established.

Proviral cDNA inserts were then recovered from genomic DNA of the infected cells. A PCR amplification was performed for this purpose whereby specific retroviral primers which flank the cloning site in the plasmid vector were employed. In this way it was possible to isolate a cDNA insert of approximately 3 kBp.

A sequence analysis revealed that this insert identified an isoform of a previously cloned gene. The previously cloned gene belonged to the mucin family and coded for MGC-24. This gene was fully identified by Masuzawa et al., J. Biochem. 112, 609–615 (1992).

The isoform now identified was designated MGC-24v and classified as CD164 (Zannettino et al., "CD164 Workshop Panel Report", in: Leucocyte Typing VI, Kishimoto, T., et al., Garland Publishing, New York (in press)).

A cell line stably transfected with the CD164-specific cDNA was used in the screening method for the production of the hybridoma cells producing antibody 67D2.

EXAMPLE 3

Cross-Blocking of CD164-Specific Monoclonal Antibodies

Three different monoclonal CD164-specific antibodies were used in a cross-blocking experiment in order to analyze whether these antibodies detect similar or different epitopes on the CD164 glycoprotein.

The antibodies were antibody 103B2 subject matter of DE 195 30 272, antibody 105A5 subject matter of DE 195 30 273 C1 as well as the inventive antibody 67D2.

As antigen the MOLM-1 cell was used (Matsuo Y., et al., Establishment and Characterization of Novel Megakaryoblastoid Cell Line, MOLM-1, from a Patient with Chronic Myelogenous Leukemia (1991)", Human Cell, 4: 261–264). This cell line has a high expression of CD164 glycoprotein on its cell surface.

Antibodies 103B2, 105A5 and 67D2 as well as a negative control antibody having in each case the same isotype were, separated from each other, incubated for thirty minutes on ice with MOLM-1 cells. Then, the cells were rinsed and either for a positive control incubated with the same monoclonal antibody or with a further CD164 antibody in order to determine blocking or non-blocking. Then, the cells were incubated with a PE-conjugated anti-IG-antibody binding to the CD164-specific monoclonal antibodies. Thereupon the samples were analyzed in the FACSCalibur flow cytometer.

Table 1 shows the result of these tests, the blocking being expressed in percentage. Percent blocking was calculated according to the following formula:

100−[(median fluorescence of cells stained with test antibody after incubation with blocking antibody)

−(median fluorescence of cells stained with isotype matched negative control antibody)]

/[(median fluorescence of cells stained with test antibody after incubation with negative control antibody)

−(median fluorescence of cells stained with isotype matched negative control antibody)]·100.

TABLE 1

Cross-blocking of CD164-specific monoclonal anti-bodies

| CD164-specific test antibody | % Blocking of CD164-specific test antibody binding by: | | |
|---|---|---|---|
| | 103B2 | 105A5 | 67D2 |
| 103B2 | — | 0% | 3.5% |
| 105A5 | 60.4% | — | 0% |
| 67D2 | 13.5% | 3.5% | — |

Table 1 reveals that after incubation of MOLM-1 cells with antibody 103B2 neither binding of antibody 105A5 nor binding of antibody 67D2 is blocked to a significant amount. This means that antibody 103B2 recognizes an epitope distinct from the epitope recognized by 105A5 as well as by 67B2.

If the epitopes were not distinct from each other, 105A5 and 67B2 could not bind to the MOLM-1 cells, too.

After incubation of MOLM-1 cells with antibody 105A5 a partial blocking of binding of 103B2 of about 60% could be shown, whereas for antibody 67D2 no blocking could be shown.

In case the MOLM-1 cells were first incubated with antibody 67D2 and thereafter with antibody 103B2 and 105A5, respectively, in no case a significant blocking of the binding of the second antibody could be detected.

Thus, antibody 103B2 does not block the binding of antibody 105A5 or 67D2 to CD164 glycoprotein.

Antibody 105A5 blocks the binding of antibody 103B2 partially but not the binding of antibody 67D2.

Antibody 67D2 does not block the binding of antibodies 103B2 and 105A5 to CD164.

As a whole it can be seen that the three different CD164-specific monoclonal antibodies recognized distinct epitopes of the CD164 glycoprotein.

What is claimed is:

1. A monoclonal antibody specific against CD164, characterized in that it is produced and released by hybridoma cells that are deposited under No. DSM ACC2303 at the German Collection of Microorganisms and Cell Cultures Ltd., DSMZ, and is designated "67D2".

2. Hybridoma cells, deposited under No. DSM ACC2303 at the German Collection of Microorganisms and Cell Cultures Ltd., DSMZ.

3. A composition comprising an antibody according to claim 1, and a pharmaceutically acceptable carrier.

4. A composition according to claim 3, wherein the antibody is coupled to a therapeutical agent.

5. A composition according to claim 3, wherein the antibody is coupled to a diagnostic agent.

6. A kit comprising an antibody according to claim 1.

* * * * *

UNITED STATES PATENT AND TRADEMARK OFFICE
CERTIFICATE OF CORRECTION

PATENT NO : 6,143,296
DATED : November 7, 2000
INVENTOR(S) : Dr. Hans-Jörg Bühring and Dr. Suzanne M. Watt It is certified that error appears in the above-identified patent and that said Letters Patent is hereby corrected as shown below:

On title page,
 [73] Assignee: Eberhard-Karls-Universität Tübingen
  Germany

Signed and Sealed this

Twenty-ninth Day of May, 2001

Attest:

NICHOLAS P. GODICI

Attesting Officer  Acting Director of the United States Patent and Trademark Office